(12) United States Patent
Zhao et al.

(10) Patent No.: US 12,376,968 B2
(45) Date of Patent: Aug. 5, 2025

(54) POST-BONE-GRAFTING EXPANDABLE CAGE

(71) Applicant: Shanghai Reach Medical Instrument Co., Ltd., Shanghai (CN)

(72) Inventors: Hongwei Zhao, Shanghai (CN); Lulu Han, Shanghai (CN); Xiaomin Huang, Shanghai (CN)

(73) Assignee: Shanghai Reach Medical Instrument Co., Ltd., Shanghai (CN)

( * ) Notice: Subject to any disclaimer, the term of this patent is extended or adjusted under 35 U.S.C. 154(b) by 0 days.

(21) Appl. No.: 17/920,026

(22) PCT Filed: Jan. 7, 2022

(86) PCT No.: PCT/CN2022/070665
§ 371 (c)(1),
(2) Date: Oct. 20, 2022

(87) PCT Pub. No.: WO2023/015839
PCT Pub. Date: Feb. 16, 2023

(65) Prior Publication Data
US 2024/0293235 A1    Sep. 5, 2024

(30) Foreign Application Priority Data

Aug. 10, 2021 (CN) .......................... 202110914152.2
Dec. 9, 2021 (CN) .......................... 202111496485.4

(51) Int. Cl.
*A61F 2/44* (2006.01)
*A61F 2/30* (2006.01)
*A61F 2/46* (2006.01)

(52) U.S. Cl.
CPC .... *A61F 2/447* (2013.01); *A61F 2002/30398* (2013.01); *A61F 2002/305* (2013.01);
(Continued)

(58) Field of Classification Search
CPC ......................................... A61F 2/4455–2/447
See application file for complete search history.

(56) References Cited

U.S. PATENT DOCUMENTS 7,828,848 B2 * 11/2010 Chauvin ............... A61F 2/4601
606/313
8,932,358 B1     1/2015 Nehls
(Continued)

FOREIGN PATENT DOCUMENTS

CN    106726020 A    5/2017
CN    109758272 U    5/2019
(Continued)

OTHER PUBLICATIONS

International Search Report, issued in PCT/CN2022/070665, dated Apr. 26, 2022.
(Continued)

*Primary Examiner* — Julianna N Harvey
(74) *Attorney, Agent, or Firm* — Zhu Lehnhoff LLP (57) ABSTRACT

A post-bone-grafting expandable cage includes a main body, a blade assembly fitted to the main body, and a pushing assembly fitted to the blade assembly, wherein an end cover is interference-fitted on one end face of the main body. The main body comprising a screw section, a side section integrally connected to two ends of the screw section respectively, and an opening section integrally connected to the side section. The pushing assembly includes a first U-shaped base and a threaded rod fixedly connected to the first U-shaped base. The threaded section of the threaded rod extends out of an end face of the first U-shaped base, a square cylindrical section of the threaded rod penetrates the first U-shaped base. The threaded section of the threaded rod
(Continued)

is threadedly matched with the threaded through-hole, and the first U-shaped base is provided in a fitting manner with the blade assembly.

6 Claims, 5 Drawing Sheets

(52) U.S. Cl.
CPC ............... *A61F 2002/30556* (2013.01); *A61F 2002/30579* (2013.01); *A61F 2002/30593* (2013.01); *A61F 2002/4627* (2013.01)

(56) References Cited

U.S. PATENT DOCUMENTS

| | | | |
|---|---|---|---|
| 2013/0006361 A1 | 1/2013 | Glerum | |
| 2013/0023994 A1* | 1/2013 | Glerum | A61F 2/447 623/17.16 |
| 2015/0012097 A1* | 1/2015 | Ibarra | A61F 2/447 623/17.15 |
| 2015/0173917 A1* | 6/2015 | Radcliffe | A61F 2/446 623/17.16 |
| 2015/0182346 A1* | 7/2015 | Emerick | A61F 2/447 29/525.01 |
| 2015/0342749 A1* | 12/2015 | Baynham | A61F 2/447 623/17.16 |
| 2019/0110902 A1* | 4/2019 | Vigliotti | A61F 2/447 |
| 2019/0388232 A1 | 12/2019 | Purcell et al. | |
| 2022/0133493 A1* | 5/2022 | Josse | A61B 17/8886 623/17.11 |

FOREIGN PATENT DOCUMENTS

| | | |
|---|---|---|
| CN | 110353862 A | 10/2019 |
| CN | 1116116844 A | 9/2020 |
| CN | 11210836 A | 12/2020 |
| CN | 113101018 A | 7/2021 |
| CN | 213607205 U | 7/2021 |
| CN | 113509295 A | 10/2021 |

OTHER PUBLICATIONS

Written Opinion, issued in PCT/CN2022/070665, dated Apr. 26, 2022.
Search Report, issued in CN202111496485.4 (priority application), by CNIPA, dated Aug. 10, 2021.
Examination Report, issued in CN202111496485.4 (priority application), by CNIPA, dated Aug. 10, 2021.

* cited by examiner

POST-BONE-GRAFTING EXPANDABLE CAGE

TECHNICAL FIELD

The present disclosure relates to the technical field of cages, and more particularly, to a post-bone-grafting expandable cage.

BACKGROUND

Degenerative spine disease is a common condition, among which lumbar degenerative spondylolisthesis, segmental instability, discogenic diseases, traumatic spondylolisthesis, etc. are generally treated by lumbar fixation and fusion. The application of interbody cage can maintain the height of intervertebral space, restore the support of anterior and middle column, increase the capacity of intervertebral foramen, relieve the compression of nerve root, prevent the collapse of intervertebral space and the formation of pseudoarthrosis. With the development of minimally invasive surgery, there is a higher demand for the design of interbody cage. On the other hand, with the application of endoscopic technology in surgery, minimally invasive surgery of spine has been gradually developed, and conventional spinal fusion surgery has been gradually minimally invasive with the assistance of endoscope. However, at present, most of the cages are conventional with fixed model and size, and it is difficult to achieve continuous adjustment of size, and it is difficult to place large cages under endoscope channel. Otherwise, the cage with adjustment function still adopts a manner of bone grafting in the cage first, wherein after the intervertebral space is implanted and the height is adjusted to be high, the bone grafting chamber becomes larger. In this way, the bone quantity implanted becomes insufficient and cannot be supplemented, so that the fusion effect is affected due to insufficient bone grafting in the cage.

SUMMARY OF THE INVENTION

It is an object of the present disclosure to provide a post-bone-grafting expandable cage. The cage is placed in the intervertebral space and adjusted in height according to the height of intervertebral space, and then the cage is used for bone grafting (i.e. posterior bone grafting). The present disclosure fundamentally solves the problem that the existing cage with an adjustable height cannot achieve sufficient bone grafting. The cage has a novel structure, is easy to operate, and has a large space for bone grafting chamber. Through the large opening at the tail of the cage, in combination with the matched special bone grafting tool, it can be ensured that the autologous bone and allogeneic bone can be easily filled into the bone grafting chamber of the cage after the cage is implanted and stretched.

The posterior bone grafting of the present disclosure, in order to achieve the above-mentioned objects and other advantages of the present disclosure, provides a cage with an adjustable height, comprising:

a main body, a blade assembly fitted to the main body, and a pushing assembly fitted to the blade assembly, wherein an end cover is interference-fitted on one end face of the main body, the main body comprising a screw section, a side section integrally connected to two ends of the screw section respectively, and an opening section integrally connected to the side section, where a threaded through-hole is provided on the screw section, and an opening through-hole is provided on the opening section, a central axis of the opening through-hole and a central axis of the threaded through-hole being located at same height position, the pushing assembly comprising a first U-shaped base and a threaded rod fixedly connected to the first U-shaped base, wherein the threaded section of the threaded rod extends out of an end face of the first U-shaped base, a square cylindrical section of the threaded rod penetrates the first U-shaped base and extends out of an end face, away from the threaded section, of the first U-shaped base, a pin is fixedly connected to an end, close to the threaded rod, of the first U-shaped base and a position of the pin is perpendicular to the axial direction of the threaded rod, the threaded section of the threaded rod being threadedly matched with the threaded through-hole, and the first U-shaped base being provided in a fitting manner with the blade assembly.

Preferably, the side section is provided with a limiting sliding groove, and a position of a central axis of the limiting sliding groove is at a same height as a central line of the threaded through-hole of the main body.

Preferably, the first U-shaped base comprises a first end plate, a first side plate integrally connected to both ends of the first end plate, a slider obliquely fixed to the first side plate, and a stopper fixed to the first side plate, wherein the stopper and the first side plate are vertically arranged, and the stopper extends from an inner wall of the first side plate in a direction of the slider and extends out of the first side plate.

The stopper cooperates with the limiting sliding groove on the main body.

Preferably a fitting groove is formed on an opposite wall of the open through-hole, and a first thread is formed on the inner wall, on the fitting groove, of the open through-hole.

Preferably, an end cover is interference-fitted on the opening section, the end cover comprising an arc-shaped plate with a through-hole opened in middle and an elastic piece integrally connected to the arc-shaped plate, an elastic piece being integrally connected to an opposite side edge of the arc-shaped plate, the elastic piece being interference-fitted with a fitting groove, a connecting section being provided on the end cover, the connecting section being used for cooperating with a workpiece to be used.

Preferably, four sliders are fixedly connected to the first side plate, and two first sliders are provided at an upper end of the first side plate, the two first sliders being obliquely fixed to the first side plate in the same oblique direction, and one end of the first sliders extending out of the first side plate.

Preferably, two second sliders are provided at a lower end of the first side plate, the two second sliders are obliquely fixed to the first side plate in the same oblique direction, and one end of the second slider extends out of the first side plate, the second slider and the first slider being symmetrically provided on the two first side plates about a horizontal central line of the first side plate, and the second slider and the first slider being at an angle with respect to the main axis thereof.

Preferably, the blade assembly comprises a first blade and a second blade symmetrically arranged and fitted with the main body, the first blade comprising a first blade tooth with a hole in middle and a first connecting enclosure plate fixedly connected to the first blade tooth, one end, close to the opening section, of the first connecting enclosure plate being provided with a first matching hole.

Preferably, the second blade comprises a second blade tooth with a hole in the middle and a second connecting enclosure plate fixedly connected to the second blade tooth, the second connecting enclosure plate being provided with a second matching hole near one end of the opening section.

Preferably, a first slider groove is symmetrically provided on an opposite side of the first connecting enclosure plate, the first slider groove being matched with the first slider, and a second slider groove is symmetrically provided on an opposite side of the second connecting enclosure plate, the second slider groove being matched with the second slider, and the first slider groove and the second slider groove being inclined at an angle to the horizontal centerline of the main body.

The two side sections are respectively provided with a fixing hole, the fixing hole is internally fixed with a stopper, a snap groove being provided on one end, close to the end cover, of the side section, a snap hole being provided in the snap groove, a displacement groove being provided on an end face, corresponding to the stopper, of the first U-shaped base, the stopper being located in the displacement groove to move, and a stabilizing rod being fixedly connected between the two first U-shaped bases.

Preferably, the end cover comprises a straight section, a snap section fixed to both ends of the straight section, and a snap integrally connected to the snap section, the snap matching a snap hole.

The advantageous effects of the present disclosure compared to the prior art are as follow.

(1) By placing the height-adjustable threaded rod at the opposite end of the opening section of the main body and adjusting the height, the space of the bone grafting chamber in the main body of the cage is released to the maximum extent, increasing the amount of bone graft, which is more conducive to bone fusion.

(2) The structure design and operation of the cage is convenient and simple, the space of the bone grafting chamber in the main body is large, and the tail of the cage has a large opening, so that it can ensure that after the cage is implanted, the autologous bone and allogeneic bone can be better filled into the bone grafting chamber in the main body of the cage. Due to the release of the space of the bone grafting chamber and the large opening of the tail, it can better cooperate with the endoscope for operation, so that the operation is more accurate and faster.

(3) The cover is designed to be sealed, after the bone graft in the main body main body has been filled with bone, the cover plate is used to seal the bone grafting chamber in the main body, ensuring that the implanted bone is confined in the cage.

DETAILED DESCRIPTION OF THE PREFERRED EMBODIMENTS

The technical solutions of the embodiments of the present disclosure will now be described more clearly and fully hereinafter with reference to the accompanying drawings. It is to be understood that the embodiments described are only a few, but not all embodiments of the invention. On the basis of the embodiments of the present disclosure, all other embodiments obtained by a person of ordinary skill in the art without inventive effort fall within the scope of the present disclosure.

With reference to FIGS. 1-5, a height-adjustable cage includes: a main body 1, a blade assembly 2 embedded in the main body 1, and a pushing assembly 3 fitted with the blade assembly 2, wherein an end cover 4 is interference-fitted on one end surface of the main body 1. When the blade assembly 2 is in a closed state, a cage is placed into a space of a vertebral body via a cage holder. The main body 1 comprises a screw section 11, a side section 12 integrally connected to two ends of the screw section 11 respectively, and an opening section 14 integrally connected to the side section 12, wherein the screw section 11 is provided with a threaded through-hole, the opening section 14 is provided with an opening through-hole, and the central axis of the opening through-hole and the central axis of the threaded through-hole are located at the same height position. The pushing assembly 3 comprises a first U-shaped base 33 and a threaded rod 31 fixedly connected to the first U-shaped base 33, wherein a threaded section of the threaded rod 31 extends out of an end face of the first U-shaped base 33. A square cylindrical section of the threaded rod 31 penetrates the first U-shaped base 33 and extends out of an end face, away from the threaded section, of the first U-shaped base 33. A pin 32 is fixedly connected to an end, close to the threaded rod 31, of the first U-shaped base 33, and the position of the pin 32 is perpendicular to an axial direction of the threaded rod 31. The threaded section of the threaded rod 31 is threadedly matched with the threaded through-hole, and the first U-shaped base 33 is fitted with the blade assembly 2. A matched tool is used to be matched with the threaded rod 31. The threaded rod 31 is driven to rotate so that the threaded rod 31 is displaced in the threaded through-hole, and then the first U-shaped base 33 is driven to move in a linear direction so that the blade assembly 2 moves towards each other in a vertical direction. The cage is expanded to reach the height required by the patient. The tool matched for expanding is withdrawn. The main body 1 and the blade assembly 2 form a larger bone grafting chamber. An instrument is then used to implant the autogenous bone or allogeneic bone into the bone grafting chamber through the opening section 14 to fill the cavity of the cage. When the bone grafting is completed, the end cover 4 is interference-fitted with the opening section 14 to block the main body 1 of the cage.

Furthermore, a limiting sliding groove 13 is provided on the side section 12, and the position of the central axis of the limiting sliding groove 13 is located at the same height position as the central line of the threaded through-hole of the main body 1. When the cage achieves the expanding function, the first U-shaped base 33 moves in an axial direction to limit the position. A fitting groove 16 is provided on an opposite inner wall of the opening through-hole, and first threads 15 are provided on both inner walls, located in the fitting groove 16, of the opening through-hole. When the cage needs to be removed or adjusted in position later, a tool is used to cooperate with the first threads 15 so as to adjust the position of the cage using the tool, so that a doctor can accurately and quickly position the cage.

Figure 1:
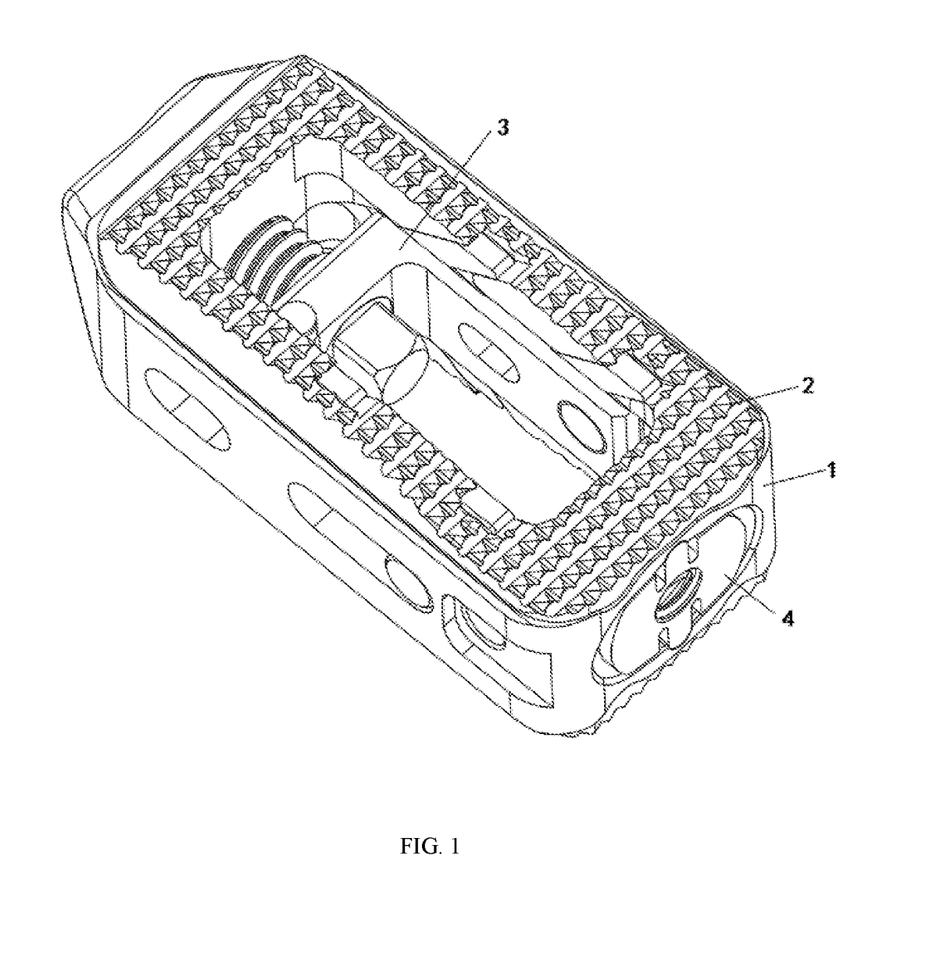
FIG. 1 is a schematic view showing a three-dimensional structure of a height-adjustable cage according to the present disclosure.
Figure 2:
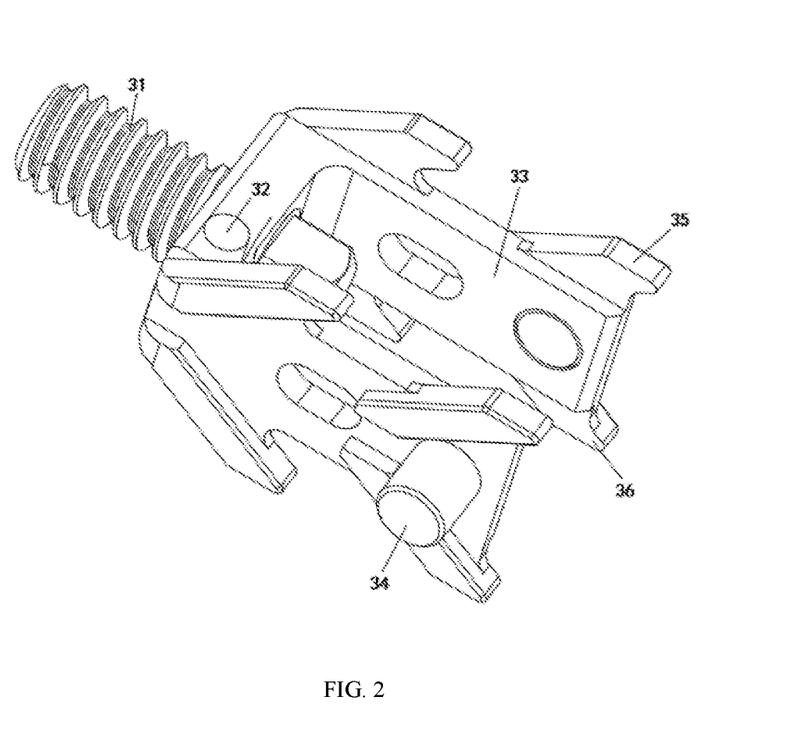
FIG. 2 is a schematic view showing the three-dimensional structure of the pushing assembly of the height-adjustable cage according to the present disclosure.

Furthermore, the first U-shaped base 33 comprises a first end plate, a first side plate integrally connected to two ends of the first end plate, a slider 35 obliquely fixed on the first side plate, and a stopper 34 fixed on the first side plate, wherein the stopper 34 and the first side plate are arranged perpendicular to each other. The stopper 34 extends from the inner wall of the first side plate in the direction of the slider 35 and extends out of the first side plate. Four sliders are fixedly connected on the first side plate, and two first sliders 35 are arranged on an upper end of the first side plate. The two first sliders 35 are obliquely fixed on the first side plate in the same oblique direction. One end of the first sliders 35 extends out of the first side plate. Two second sliders 36 are provided at the lower end of the first side plate. The two second sliders 36 are obliquely fixed on the first side plate in the same oblique direction. One end of the second sliders 36 extends out of the first side plate, and the second sliders 36 and the first sliders 35 are symmetrically provided on the two first side plates about a horizontal central line of the first side plate. The second slider 36 and the first slider 35 are at an angle with respect to the main axis thereof.

Figure 3:
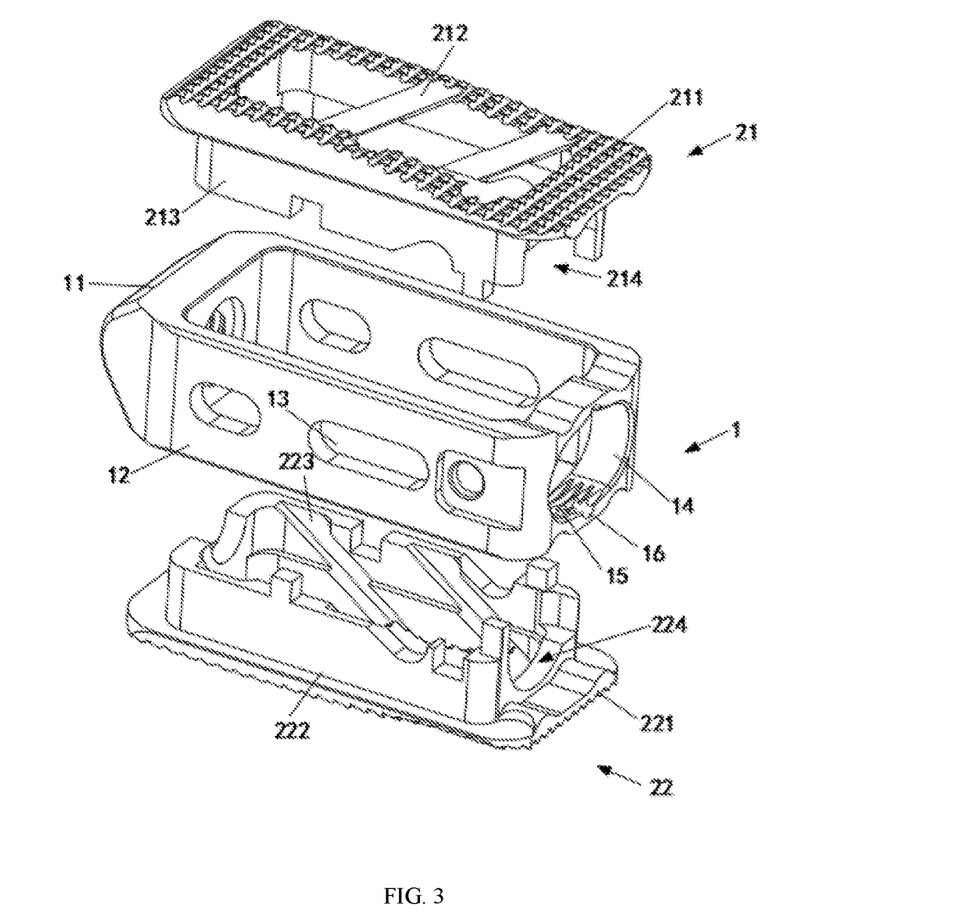
FIG. 3 is a schematic view showing a three-dimensional explosive structure of a blade assembly of the height-adjustable cage according to the present disclosure.
Figure 4:
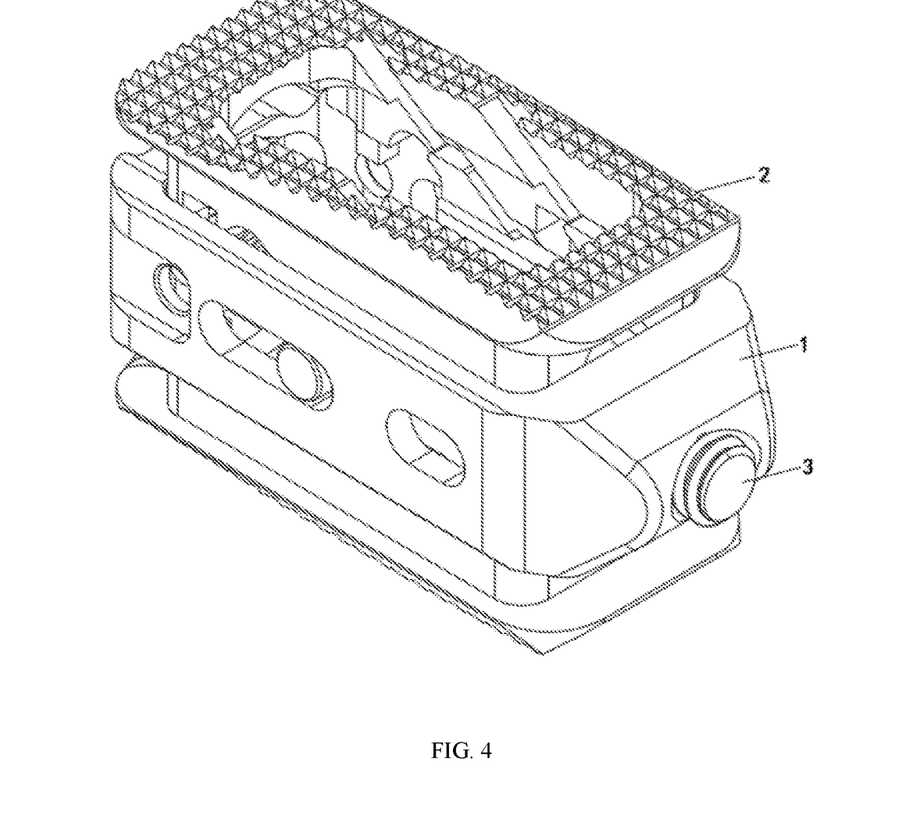
FIG. 4 is a schematic view showing a three-dimensional explosive structure of a blade assembly of a height-adjustable cage according to the present disclosure, wherein the cage is expanded in an operation state.

Furthermore, the blade assembly 2 comprises a first blade 21 and a second blade 22 which is symmetrical and fitted to the main body 1. The first blade 21 comprises a first blade tooth 211 with a hole in the middle and a first connecting enclosure plate 213 fixedly connected to the first blade tooth 211. One end, close to the opening section 14, of the first connecting enclosure plate 213 is provided with a first matching hole 214. The blade tooth structure is not limited to a sharp-tined and pyramid-shaped array form. The second blade 22 comprises a second blade tooth 221 with a hole in the middle and a second connecting enclosure plate 222 fixedly connected to the second blade tooth 221. One end, close to the opening section 14, of the second connecting enclosure plate 222 is provided with a second matching hole 224. A first slider groove 212 is symmetrically provided on an opposite side face of the first connecting enclosure plate 213, and the first slider groove 212 matches the first slider 35. A second slider groove 223 is symmetrically provided on an opposite side face of the second connecting enclosure plate 222, and the second slider groove 223 matches the second slider 36. The first slider groove 212 and the second slider groove 223 form an inclined angle with the horizontal central line of the main body 1. When a tool is used for clamping with the threaded rod 31, the blade assembly 2 is driven to move in a linear direction. At this time, the first slider 35 and the second slider 36 respectively slide along the first slider groove 212 and the second slider groove 223. Since the first slider groove 212 and the second slider groove 223 are in an inclined state, when the first slider 35 and the second slider 36 respectively move in the first slider groove 212 and the second slider groove 223, by means of the interaction force between the first slider 35 and the second slider 36 with the first slider groove 212 and the second slider groove 223, the first U-shaped base 33 is subjected to a pushing force along the vertical side, thereby moving the first blade 21 and the second blade 22 away from the main body 1, respectively.

Furthermore, the opening section 14 is interference-fitted with an end cover 4. The end cover 4 comprises an arc-shaped plate provided with a through-hole in the middle and an elastic piece integrally connected to the arc-shaped plate. The elastic piece is integrally connected to an opposite side edge of the arc-shaped plate. The elastic piece is interference-fitted with the fitting groove 16, and the end cover 4 is provided with a connecting section. The connecting section is used for matching with a workpiece to be used.

Figure 5:
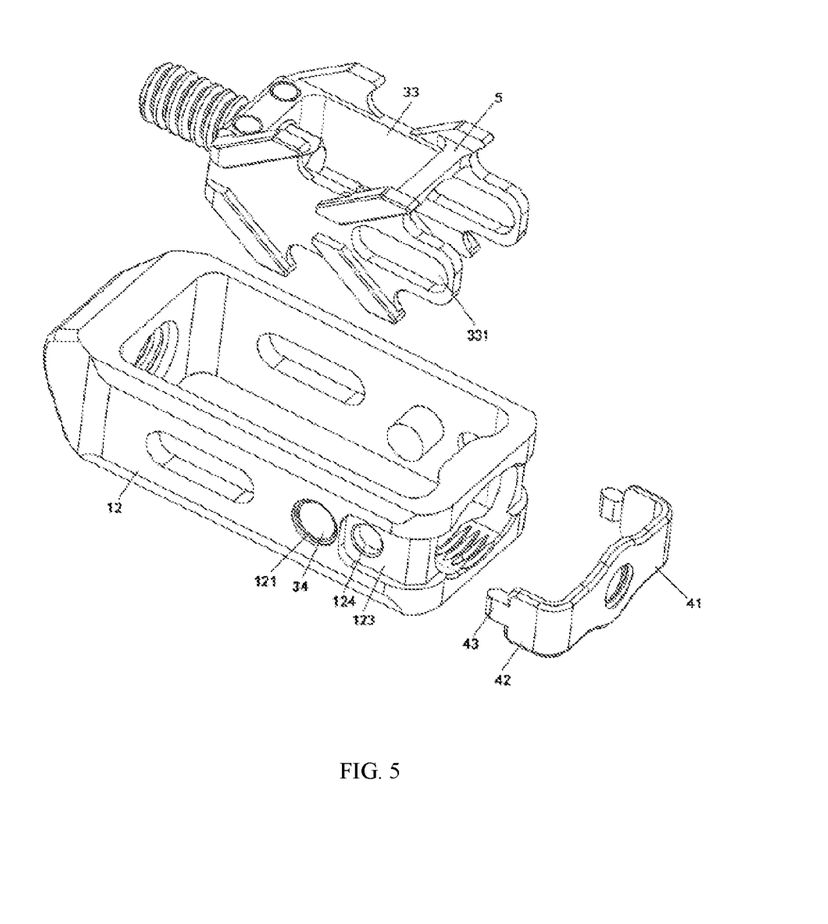
FIG. 5 is a schematic view showing a three-dimensional explosive structure of a cage of a blade assembly of a height-adjustable cage according to the present disclosure.

With reference to FIG. 5, the two side sections 12 are respectively provided with a fixing hole 121, and the fixing hole 121 is internally fixed with the stopper 34. One end, close to the end cover 4, of the side section 12 is provided with a snap groove 123, and a snap hole 124 is provided in the snap groove 123. A displacement groove 331 is provided on an end face, corresponding to the stopper 34, of the first U-shaped base 33. The stopper 34 is located in the displacement groove 331 for movement, and a stabilizing rod 5 is fixedly connected between the two first U-shaped bases 33. By rotating the threaded rod 31, the stopper 34 is located in the displacement groove 331 to move in a horizontal direction. The movement of the overall structure is more stable, and the stabilizing rod 5 is provided between the first U-shaped bases 33 so that the structural strength of the first U-shaped bases 33 is increased.

With reference to FIG. 5, the end cover 4 comprises a straight section 41, a snap section 42 fixed at two ends of the straight section 41, and a snap 43 integrally connected to the snap section 42. The snap 43 matches a snap hole 124, and the end cover 4 is snapped to the snap hole 124 via the snap 43, so that the end cover 4 is more firmly connected to the side section 12.

The number of equipment and process scales described herein are intended to simplify the description of the invention, and applications, modifications and variations of the invention will be apparent to those skilled in the art.

While the embodiments of the present disclosure have been disclosed above, it is not intended to be limited to the applications set forth in the specification and the embodiments, but capable of use in various fields which the present disclosure is applicable for. Other changes and modifications may be readily made by those skilled in the art. Therefore, without departing from the generic concept as defined by the appended claims and their equivalents, the present disclosure is not limited to the details and examples shown herein.

The invention claimed is:

1. A post-bone-grafting expandable cage comprising:
a main body having first and second lengthwise ends, a screw section at the first lengthwise end of the main body having a threaded hole formed therein, an opening section at the second lengthwise end of the main body having a through hole axially aligned with the threaded hole at the first lengthwise end and through which a tool can be inserted into the main body to expand and contract the cage, and first and second side plates disposed on opposite widthwise sides of the main body and extending between the first and second lengthwise ends of the main body;
first and second blades slidably supported by the main body for movement towards and away from each other in a vertical direction of the main body to adjust a height of the cage, each of the blades having an outer surface with teeth formed thereon and first and second enclosure plates extending in a lengthwise direction of the blades and projecting perpendicularly from the outer surface of the blade into an interior of the main body, each of the enclosure plates of the first blade having a pair of upper slider grooves formed in an interior surface thereof, and each of the enclosure plates of the second blade having a pair of lower slider grooves formed in an interior surface thereof, each of the slider grooves extending diagonally with respect to a lengthwise direction of the enclosure plate in which it is formed, the upper slider grooves sloping in an opposite direction from the lower slider grooves;

a pushing assembly slidably disposed within the main body for translation in a lengthwise direction of the main body and comprising a U-shaped base having first and second lengthwise ends, an end wall at the first lengthwise end of the U-shaped base, and first and second side plates extending in a lengthwise direction of the U-shaped base away from the end wall, the second lengthwise end of the U-shaped base being completely open with no connection between the side plates at the second lengthwise end of the U-shaped base, the pushing assembly including a threaded rod rotatably supported by the end wall of the pushing assembly for rotation about an axis of the threaded rod and having a threaded portion threadingly engaged with the threaded hole in the screw section of the main body, each of the side plates of the U-shaped base including two elongated upper sliders and two elongated lower sliders, each of the sliders being disposed on an outer side of one of the side plates, each of the two upper sliders extending above a top surface of the side plate on which it is disposed, and each of the two lower sliders extending below a lower surface of the corresponding side plate on which it is disposed, each of the sliders being slidably disposed in a different one of the slider grooves in the first and second blades; and an end cover which is detachably mounted on the second lengthwise end of the main body over the through hole in the opening section.

2. The post-bone-grafting expandable cage as claimed in claim 1, wherein the first and second side plates of the U-shaped base are unconnected to each other between the end wall and the second lengthwise end of the U-shaped base.

3. The post-bone-grafting expandable cage as claimed in claim 1, wherein the end cover is mounted on the second lengthwise end of the main body with an interference fit.

4. The post-bone-grafting expandable cage as claimed in claim 1 including a pin extending upwards from the end wall of the U-shaped base perpendicular to an axis of the threaded rod.

5. The post-bone-grafting expandable cage as claimed in claim 1, wherein each blade includes a through hole in its outer surface surrounded by the teeth formed on its outer surface.

6. The post-bone-grafting expandable cage as claimed in claim 1, wherein an elongated groove is formed in one of the side plates of the main body, and the pushing assembly includes a stopper extending outwards from one of the side plates of the U-shaped base and extending into the elongated groove.

* * * * *